US011228661B2

(12) United States Patent
Luo et al.

(10) Patent No.: US 11,228,661 B2
(45) Date of Patent: Jan. 18, 2022

(54) AIR QUALITY DETECTION APPARATUS, AIR QUALITY DATA PROCESSING METHOD, AND SERVER (71) Applicant: Tencent Technology (Shenzhen) Company Limited, Shenzhen (CN)

(72) Inventors: Xiaosong Luo, Shenzhen (CN); Wenbin Yang, Shenzhen (CN); Juan Wen, Shenzhen (CN); Xiaohong Ding, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 306 days.

(21) Appl. No.: 15/785,257

(22) Filed: Oct. 16, 2017

(65) Prior Publication Data
US 2018/0041606 A1  Feb. 8, 2018

Related U.S. Application Data (63) Continuation-in-part of application No. PCT/CN2016/082417, filed on May 17, 2016.

(30) Foreign Application Priority Data

Nov. 3, 2015  (CN) .......................... 201510740464.0

(51) Int. Cl.
*H04L 29/08* (2006.01)
*G01D 21/00* (2006.01)
*G01N 33/00* (2006.01)
(52) U.S. Cl.
CPC ............. *H04L 67/32* (2013.01); *G01D 21/00* (2013.01); *G01N 33/0027* (2013.01); *H04L 67/12* (2013.01)

(58) Field of Classification Search
CPC ......... G01D 21/00; H04L 67/32; H04L 67/12; G01N 33/0027
See application file for complete search history.

(56) References Cited

U.S. PATENT DOCUMENTS

2006/0090542 A1   5/2006  Nakano
2013/0080053 A1*  3/2013  Rakshit .............. G01C 21/3461
                                                        701/527

(Continued)

FOREIGN PATENT DOCUMENTS

CN         1409278 A     4/2003
CN       101523199 A     9/2009

(Continued)

OTHER PUBLICATIONS

EPA Air Sensor Guidebook, Jun. 2014 (Year: 2014).*

(Continued)

*Primary Examiner* — Brent A. Fairbanks
(74) *Attorney, Agent, or Firm* — Morgan, Lewis & Bockius LLP (57) ABSTRACT A method of processing air quality data includes: receiving air indicator data collected by one or more air quality sensors, wherein the one or more air quality sensors are detachably coupled to a hardware base of the air quality monitoring station via one or more data communication interfaces, and the hardware base is communicably coupled to a remote server over a network; generating air quality data according to the air indicator data, wherein the air quality data is derived from air indicator data received from one or more air quality sensors over a distance traveled by the one or more air quality sensors; and sending the air quality data, via the hardware base, to the remote server.

17 Claims, 4 Drawing Sheets (56) References Cited

U.S. PATENT DOCUMENTS

2016/0318368 A1* 11/2016 Alger ................. G01C 21/3453
2017/0166217 A1* 6/2017 Sbianchi ............... H04B 1/1036
2017/0272338 A1* 9/2017 Borrel ................... H04W 4/023

FOREIGN PATENT DOCUMENTS

| CN | 101888380 A | 11/2010 |
| CN | 102032951 A | 4/2011 |
| CN | 102812501 A | 12/2012 |
| CN | 202649217 U | 1/2013 |
| CN | 103900641 A | 7/2014 |
| CN | 104344511 A | 2/2015 |
| CN | 204165856 U | 2/2015 |
| CN | 105301196 A | 2/2016 |

OTHER PUBLICATIONS

Tencent Technology, ISR, PCT/CN2016/082417, Aug. 11, 2016, 2 pgs.
Tencent Technology, Written Opinion, PCT/CN2016/082417, dated Aug. 11, 2016, 6 pgs.
Tencent Technology, IPRP, PCT/CN2016/082417, May 8, 2018, 7 pgs.

\* cited by examiner

AIR QUALITY DETECTION APPARATUS, AIR QUALITY DATA PROCESSING METHOD, AND SERVER

RELATED APPLICATIONS

This application is a continuation-in-part application of PCT/CN2016/082417, entitled "DEVICE FOR EXAMINING AIR QUALITY, METHOD FOR PROCESSING AIR QUALITY DATA AND SERVER" filed on May 17, 2016, which claims priority to Chinese Patent Application No. 201510740464.0, filed with the State Intellectual Property Office of the People's Republic of China on Nov. 3, 2015, and entitled "AIR QUALITY DETECTION APPARATUS, AND AIR QUALITY DATA PROCESSING METHOD AND APPARATUS", both of which are incorporated herein by reference in their entirety.

FIELD OF THE TECHNOLOGY

The present disclosure relates to the field of air quality monitoring technologies, and in particular, to an air quality detection apparatus, an air quality data processing method, and a server.

BACKGROUND OF THE DISCLOSURE

As people pay more attention to air quality in life, various air quality detection methods emerge. Especially, for a private car, it is quite important to know the air quality in the car because air in the car is in a closed environment.

In conventional air quality detection methods, a desktop air quality detector is usually used for detection, and some air quality detectors further have a network connection function. However, because the conventional air quality detectors having the network connection function are generally integrated, and require complete data collection, the air quality detectors need to have multiple sensor functions. However, after collecting data for a long time, a sensor is easy to be inaccurate in detection or insensitive, and consequently, the sensor needs to be replaced or calibrated. An existing air quality detector cannot be flexibly replaced or calibrated, and can only be replaced with a new detector. Therefore, air quality detectors used in conventional technologies have relatively poor flexibility and practicality, and have higher costs.

SUMMARY

By means of an air quality detection apparatus, an air quality data processing method, and a server that are disclosed in this application, the one or more problems involved in the background are resolved. An air quality detection apparatus is provided, including: a detachable sensor component, configured to: collect air indicator data collected by one or more air quality sensors, and generate air quality data according to the indicator data; and a base, connected to the detachable sensor component, and configured to: receive the air quality data transmitted by the detachable sensor component, and upload the air quality data and a corresponding base identifier to a server by means of a network.

An air quality data processing method is provided, including: receiving air quality data and a corresponding base identifier that are uploaded by an air quality detection apparatus; parsing the air quality data, to obtain air indicator data collected by one or more air quality sensors in a detachable sensor component that is connected to a base in the air quality detection apparatus; and storing the base identifier and the corresponding one or more pieces of air indicator data.

A server is provided, including a memory and a processor, the memory storing instructions, and the instructions, when executed by the processor, causing the processor to perform the following steps: receiving air quality data and a corresponding base identifier that are uploaded by an air quality detection apparatus; parsing the air quality data, to obtain air indicator data collected by one or more air quality sensors in a detachable sensor component that is connected to a base in the air quality detection apparatus; and storing the base identifier and the corresponding one or more pieces of air indicator data.

Details of one or more embodiments of the present technology are provided in the following accompanying drawings and descriptions. Other features, objectives, and advantages of the present disclosure become apparent with reference to the specification, the accompanying drawings, and the claims.

BRIEF DESCRIPTION OF THE DRAWINGS

To describe the technical solutions of the embodiments of the present technology or the existing technology more clearly, the following briefly introduces the accompanying drawings required for describing the embodiments or the existing technology. Apparently, the accompanying drawings in the following description show only some embodiments of the present technology, and a person of ordinary skill in the art may still derive other drawings from these accompanying drawings without creative efforts.

DESCRIPTION OF EMBODIMENTS

To make an objective, technical solution, and advantage of the present disclosure clearer, with reference to accompanying drawings and embodiments, the following further makes detailed description of the present disclosure. It should be understood that, the specific embodiments described herein are merely intended for explaining the present disclosure, and are not for limiting the present disclosure.

Figure 1:
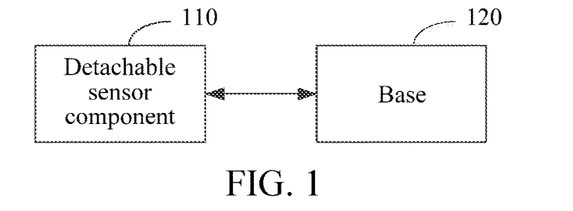
FIG. 1 is a schematic structural diagram of an air quality detection apparatus according to some embodiments.

In some embodiments, as shown in FIG. 1, an air quality detection apparatus is provided. The apparatus includes a detachable sensor component 110 and a base 120. The detachable sensor component 110 includes one or more air quality sensors. Preferably, the air quality sensors may be packaged into corresponding pluggable sensor modules, so that each sensor module can independently work, and can be integrated into the detachable sensor component 110. Similarly, the detachable sensor component 110 is connected to the base 120 preferably in a pluggable manner, so as to facilitate detachment and replacement.

The detachable sensor component 110 is configured to: collect air indicator data collected by the one or more air quality sensors, and generate air quality data according to the indicator data. The base 120 is connected to the detachable sensor component 110, and is configured to: receive the air quality data transmitted by the detachable sensor component 110, and upload the air quality data and a corresponding base identifier to a server by means of a network.

In some embodiments, the air quality sensors may include a temperature sensor, a humidity sensor, and/or the like, where the temperature sensor and the humidity sensor are respectively configured to collect temperature data and humidity data of air around the air quality detection apparatus; or may include a formaldehyde sensor, a carbon monoxide sensor, and/or the like, where the formaldehyde sensor and the carbon monoxide sensor are respectively configured to collect formaldehyde content and carbon monoxide content in the air around the air quality detection apparatus; or may include sensors configured to collect content of various flammable gases and PM 2.5, an air quality index (AQI), and other air quality indicators, and the like. Correspondingly, the air indicator data is data, for example, temperature data, humidity data, formaldehyde content data, PM 2.5 content data, or air quality index data, that is collected by the air quality sensors. Other examples are not listed herein.

The detachable sensor component 110 consolidates the air indicator data detected by the air quality sensors into the air quality data. That is, in some embodiments, the air quality data includes the air indicator data detected by all the air quality sensors in the detachable sensor component 110. The detachable sensor component 110 transmits the generated air indicator data to the base 120.

After receiving the air quality data transmitted by the detachable sensor component 110, the base 120 uploads the air quality data and a base identifier of the base 120 to the server by means of the network. The base identifier is used for uniquely identifying the air quality detection apparatus, so that the server can distinguish between and learn the air quality data detected by air quality detection apparatuses.

The base 120 in this application is a support part of the detachable sensor component 110. The one or more air quality sensors in the detachable sensor component 110 may be detachably installed on the base 120.

In this embodiment, the air quality sensors are detachable, and a corresponding air quality sensor can be selected and installed according to a user's requirement, so as to form different combinations. Therefore, the replacement is more convenient and rapid, is high in flexibility, and can reduce costs.

Figure 2:
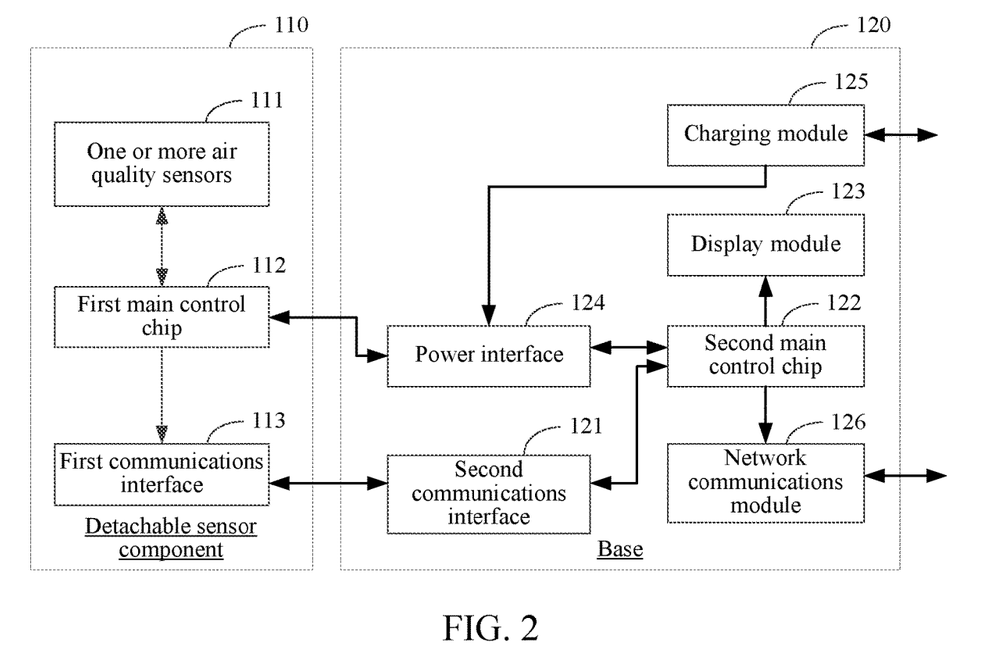
FIG. 2 is a schematic structural diagram of an air quality detection apparatus according to some embodiments.

In some embodiments, as shown in FIG. 2, the detachable sensor component 110 includes one or more air quality sensors 111, a first main control chip 112, and a first communications interface 113. The base 120 includes a second communications interface 121, a second main control chip 122, a display module 123, a power interface 124, a charging module 125, and a network communications module 126. In some embodiments, all or some of the processing functions of the first main control chip and the second main control chip are performed by a processing unit that includes one or more processor and memory storing instructions for performing the functions. In some embodiments, the processing unit includes two or more sub-processing units that are distributed on the base, the sensor component, the air quality sensors, and optionally, other components of the air quality monitoring station. In some embodiments, the air quality monitoring station is installed inside a vehicle, and monitors the air quality both inside and immediately outside of the vehicle as the vehicle travels on roads from location to location.

The one or more air quality sensors 111 are detachably installed in the detachable sensor component 110, and are connected to the first main control chip 112. The air quality sensors can respectively collect and parse corresponding air indicator data around the detachable sensor component 110. The first main control chip 112 is connected to the air quality sensors, so as to obtain the air indicator data collected by the air quality sensors, and consolidate the indicator data to generate air quality data. The first main control chip 112 is further connected to the first communications interface 113. The first communications interface 113 is connected to the second communications interface 121. Therefore, the air quality data generated by the first main control chip 112 can be transmitted to the base 120 by means of the third communications interface 113. The first main control chip 112 may be connected to the power interface 124, to obtain electric energy from the charging module 125 in the base 120, so as to control running of the detachable sensor component 110.

The base 120 obtains, by means of the second communications interface 121, the air quality data transmitted from the first communications interface 113. The second communications interface 121 is further connected to the second main control chip 122, so that the second main control chip 122 can obtain the air quality data. The second main control chip 122 is further separately connected to the display module 123, the power interface 124, and the network communications module 126 in the base 120, to control running of the base 120. The second main control chip 122 parses the obtained air quality data, to obtain the corresponding air indicator data collected by each air quality sensor, and transmit the air indicator data to the display module 123 for display. In addition, the power interface 124 is connected to the charging module 125. The charging module 125 may be connected to an in-vehicle cigar lighter for charging, and stores electric energy. The second main control chip 122 obtains the electric energy from the charging module 125 by means of the power interface 124, to control the running of the base 120. The second main control chip 122 is further connected to the network communications module 126, and uploads the air quality data and a corresponding base identifier to the server by means of the network communications module 126. The network communications module 126 may communicate with an external terminal or server by means of a wireless network. Wireless network communication includes, but is not limited to, subscriber identity module (SIM) card communication, Bluetooth communication, wireless fidelity (WiFi) communication, and the like.

Further, in some embodiments, communication between the first communications interface 113 and the second communications interface 121 may be performed in a serial communication manner. Specifically, a baud rate of communication between the first communications interface 113 and the second communications interface 121 may be set to 9600, a data bit may be set to 8 bits, a stop bit may be set to 1 bit, no parity bit is set, and the like.

Further, after obtaining, by means of parsing, the corresponding air indicator data collected by each air quality sensor, the second main control chip 122 can further determine, according to a related air quality evaluation standard, an air quality status reflected by each piece of air indicator data. Specifically, multiple thresholds may be set for each air quality indicator. When corresponding air indicator data obtained by means of parsing falls within a range between two neighboring thresholds, correspondingly, specific air quality status information indicated by the corresponding air indicator data is determined. In addition, each piece of air quality status information and air indicator data corresponding to the piece of air quality status information are both sent to the display module 123 for display.

For example a first temperature threshold, a second temperature threshold, a third temperature threshold, and a fourth temperature threshold may be set for temperature indicator data, and respectively correspond to 0° C., 15° C., 28° C., and 35° C. When a temperature is less than the first temperature threshold, between the first temperature threshold and the second temperature threshold, between the second temperature threshold and the third temperature threshold, between the third temperature threshold and the fourth temperature threshold, or greater than the fourth temperature threshold, it may be determined that specific air quality status information represented by the temperature is respectively freezing cold, cold, cool, hot, or extremely hot. For another example a first AQI threshold, a second AQI threshold, a third AQI threshold, a fourth AQI threshold, and a fifth AQI threshold may be set for an AQI indicator index, and respectively correspond to 50, 100, 150, 200, and 300. When an AQI is less than the first AQI threshold, between the first AQI threshold and the second AQI threshold, between the second AQI threshold and the third AQI threshold, between the third AQI threshold and the fourth AQI threshold, between the fourth AQI threshold and the fifth AQI threshold, or greater than the fifth AQI threshold, it may be determined that specific air quality status information represented by the AQI is respectively excellent, good, lightly polluted, moderately polluted, heavily pollution, or severely polluted. Correspondingly, information such as "AQI index: 34 (excellent); temperature: 32° C. (hot)" may be displayed.

In some embodiments, the air quality data includes protocol header data, a quantity of pieces of air indicator data, and at least one piece of air indicator data.

The protocol header data is generally a piece of fixed data, so that when receiving the air quality data, the base 120 can rapidly locate a communication protocol of the air quality data according to the protocol header data. The quantity of pieces of air indicator data is used for indicating a quantity of pieces of detected air indicator data that are included in the air quality data. Generally, a quantity of pieces of air indicator data corresponds to a quantity of sensors in a detachable sensor component.

In some embodiments, in addition to the protocol header data, the quantity of pieces of air indicator data, and the at least one piece of air indicator data, the air quality data further includes parity data. The detachable sensor component 110 is configured to generate the parity data according to the quantity of pieces of air indicator data and the at least one piece of air indicator data.

Preferably, a bit-by-bit XOR operation may be performed on the quantity of pieces of air indicator data and all the pieces of air indicator data, to obtain the parity data.

Specifically, a format of the air quality data transmitted by the detachable sensor component 110 to the base 120 is shown in Table 1. In Table 1, 1 byte is separately allocated to a protocol header (that is, the protocol header data), an indicator quantity (that is, the quantity of pieces of air indicator data), and a parity bit (that is, the parity data).

The protocol header is fixed to 0xFF. The indicator quantity is determined according to the specific quantity of pieces of air indicator data collected by the detachable sensor component 110. For example, when the detachable sensor component 110 collects five pieces of air indicator data including air temperature data, air humidity data, carbon monoxide content data, sulfur dioxide content data, and formaldehyde content data, a corresponding indicator quantity is 0x05. Correspondingly, data of an indicator 1 to data of an indicator 5 respectively correspond to the foregoing five pieces of air indicator data. The parity bit is obtained by performing an XOR operation on the indicator quantity and the data of the indicator 1 to the data of the indicator 5.

TABLE 1

| Protocol header | Indicator quantity | Data of an indicator 1 | ... | Data of an indicator 5 | Parity bit |
| --- | --- | --- | --- | --- | --- |
| 0xFF | 0x05 | | | | 0x25 |

In some embodiments, the air indicator data includes an indicator code, a unit code, a quantity of decimal places, a high-order bit of the indicator data, and a low-order bit of the indicator data.

Specifically, a data structure of data of an indicator i (that is, the air indicator data) is shown in Table 2. The indicator code, the unit code, the quantity of decimal places, the high-order bit of the indicator data, and the low-order bit of the indicator data each occupy 1 byte.

The indicator code is used for representing a corresponding gas indicator. For example, it is preset that 0x01 represents an air temperature, 0x02 represents air humidity, and 0x17 represents content of PM 2.5 in the air.

The unit code is used for representing units of different gas indicators. For example, it is preset that 0x01 represents ° C. (Celsius temperature), 0x02 represents ° F. (Fahrenheit temperature), 0x05 represents $g/m^3$ (grams per cubic meter), and 0x10 represents $ug/m^3$ (micrograms per cubic meter).

For concision of description, in specific data examples below, meanings represented by the data are all the same as the foregoing preset gas indicators and units of the gas indicators.

The quantity of decimal places represents a corresponding quantity of places following a decimal point in an indicator value. The quantity of decimal places, the high-order bit of the indicator data, and the low-order bit of the indicator data are used for reflecting an indicator value of the indicator data. Specifically, a calculation formula for the indicator value may be as follows:

an indicator value=(255*a high-order bit of indicator data+a low-order bit of the indicator data)/$10^n$, where n represents a value of the quantity of decimal places.

TABLE 2

| Indicator code | Unit code | Quantity of decimal places | High-order bit of indicator data | Low-order bit of indicator data |
| --- | --- | --- | --- | --- |
| 0x01 | 0x05 | 0x02 | 0x00 | 0x05 |

For example, if a specific piece of air indicator data is 01 01 02 0A 11, an indicator code thereof is 0x01; a unit code thereof is 0x01; a quantity of decimal places thereof is 0x02; a high-order bit of the indicator data is 0x0A; and a low-order bit of the indicator data is 0x11. Therefore, actual meaning information obtained according to the piece of air indicator data is that an air temperature is 25.77° C.

For another example, when the air quality data that is transmitted by the detachable sensor component 110 and that is received by the base 120 is specifically FF 02 01 01 02 0A 11 17 10 00 00 3C 20, it can be learned that protocol header data of the air quality data is 0xFF; an indicator quantity is 0x02; data of an indicator 1 is 01 01 02 0A 11; data of an indicator 2 is 17 10 00 00 3C; and a parity bit is 0x20. The parity bit is obtained by performing a bit-by-bit XOR operation on the indicator quantity, the data of the indicator 1, and the data of the indicator 2. In addition, it can be learned, according to the air quality data, that actual meaning data indicated by the air quality data is that an air temperature is 25.77° C. (the data of the indicator 1), and content of PM 2.5 in the air is 60 g/m³ (the data of the indicator 2).

In this embodiment, the air quality data includes the parity data, so that the server can generate, by using the same method, authentication data based on the received air quality data, and determine the accuracy of the received data by comparing the authentication data with the parity bit data.

Figure 3A:
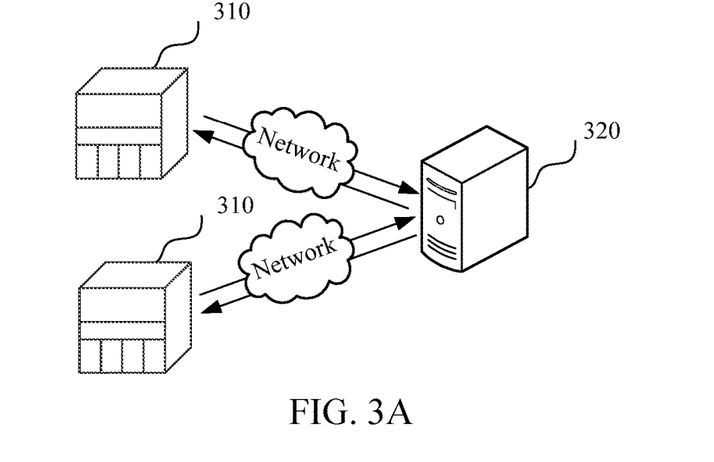
FIG. 3A is a diagram of an application environment of an air quality data processing method according to some embodiments.

An air quality data processing method provided in some embodiments of the present technology may be applied to an environment shown in FIG. 3A. Referring to FIG. 3A, an air quality detection apparatus 310 may detect quality of flowing air around the air quality detection apparatus 310 by means of one or more air quality sensors. For example, the air quality detection apparatus 310 may detect air indicator data such as air temperature data, air humidity data, and content of formaldehyde (HCHO), inhalable particulate matters (PM 10), fine particulate matters (PM 2.5), sulfur dioxide ($SO_2$), nitrogen dioxide ($NO_2$), carbon monoxide (CO), ozone ($O_3$), total suspended particulate matters (TSP), lead (Pb), fluoride, and other poisonous and harmful organic compounds in the air; generate air quality data according to all the pieces of detected air indicator data; and upload the air quality data and identifier data of the air quality detection apparatus 310 to a server 320. The identifier data is identifier data used for uniquely identifying the air quality detection apparatus 310. Preferably, the identifier data is a base identifier of the air quality detection apparatus 310. The server 320 can receive, parse, and store air quality data uploaded by each air quality detection apparatus 310, and further receives and stores identifier data of each air quality detection apparatus 310. The server 320 can distinguish, by means of the identifier data, between the air quality data correspondingly detected by the air quality detection apparatuses.

Figure 3B:
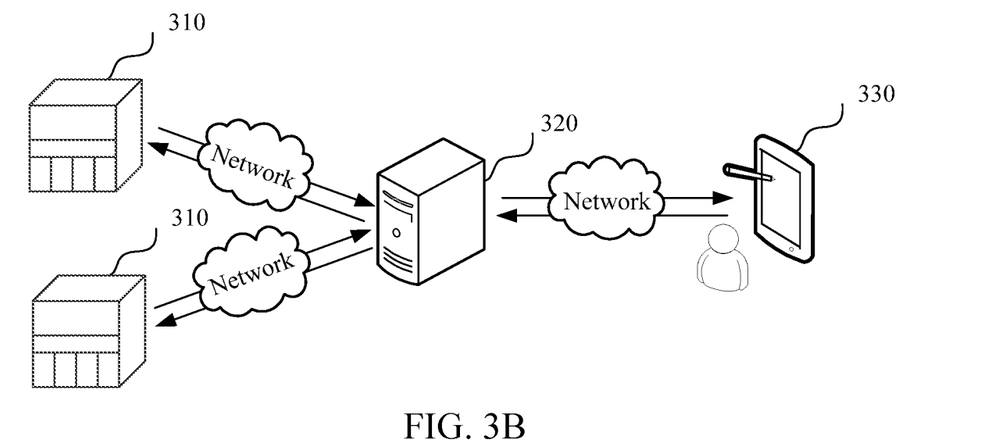
FIG. 3B is a diagram of an application environment of an air quality data processing method according to some embodiments.

Further, the air quality data processing method provided in this embodiment of the present technology may be further applied to an environment shown in FIG. 3B. Referring to FIG. 3B, the server 320 communicates with the air quality detection apparatus 310 by means of a network, and obtains, stores, and parses the air quality data and the corresponding identifier data that are uploaded by the air quality detection apparatus 310. In addition, the server 320 communicates with a terminal 330 by means of a network, receives a data query instruction sent by the terminal 330, parses the query instruction, and sends the corresponding parsed air quality data to the terminal 330. Correspondingly, the terminal 330 has an instruction sending function and an instruction receiving function. For example, the terminal 330 sends the query instruction to the server 320 by means of the network, and receives the corresponding air quality data returned by the server 320. In addition, the terminal 330 has a display function, and displays the air quality data by means of an application interface, so that users can read the air quality data. The terminal 330 includes, but is not limited to, a computer, a smartphone, a tablet computer, a wearable intelligent device, a personal digital assistant (PDA), and the like that can run applications.

Figure 4:
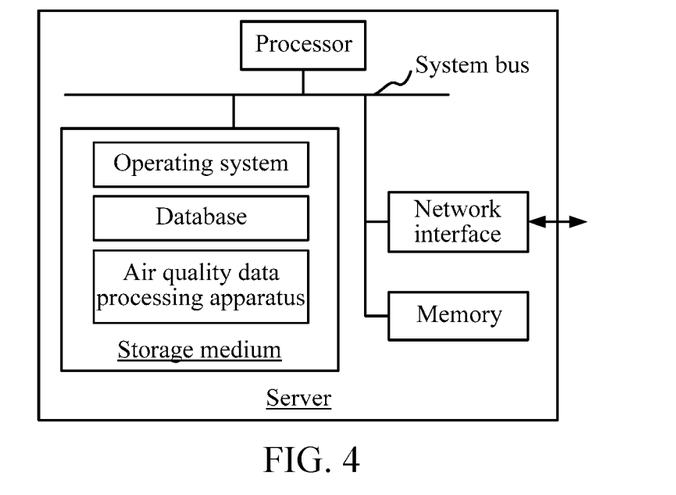
FIG. 4 is a schematic diagram of a component structure of a server according to some embodiments.

In some embodiments, an internal structure of the server 320 in FIG. 3A and FIG. 3B is shown in FIG. 4. The server 320 includes a processor, a storage medium, a memory, and a network interface that are connected by means of a system bus. The storage medium of the server 320 stores an operating system, a database, and an air quality data processing apparatus. The database is configured to store data such as air quality data and identifier data. The air quality data processing apparatus is configured to implement an air quality data processing method. The processor of the server 320 is configured to provide a calculation and controlling capability, to support running of the entire inbound traffic processing capability of the server. The memory of the server 320 provides an environment for running of the air quality data processing system in the storage medium. The network interface of the server 320 is configured to connect to and communicate with an external terminal or server by means of a network, for example, receive and store the air quality data and the identifier data that are uploaded by the air quality detection apparatus 310, or send the parsed air quality data to the terminal 330.

Figure 5:
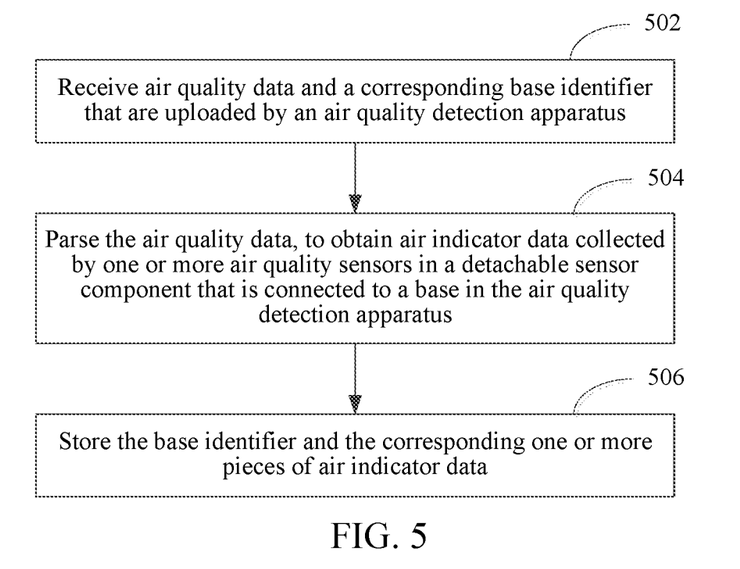
FIG. 5 is a flowchart of an air quality data processing method according to some embodiments.

As shown in FIG. 5, in some embodiments, an air quality data processing method is provided. The method may be applied to the server shown in FIG. 3A or the server in FIG. 3B, and specifically includes the following steps:

Step 502: Receive air quality data and a corresponding base identifier that are uploaded by an air quality detection apparatus.

Specifically, the server is configured to receive the air quality data and the corresponding base identifier that are uploaded by the air quality detection apparatus. The air quality data includes air indicator data collected by one or more air quality sensors in the air quality detection apparatus. Each piece of air indicator data reflects corresponding indicator information in the air, and for example, may correspondingly reflect information of a temperature and humidity in the air, or information of content of PM 2.5, formaldehyde, and some flammable gases in the air. The base identifier is used for: uniquely determining a base of the air quality detection apparatus, and correspondingly determining the air quality detection apparatus by determining the base.

In this embodiment, the server may receive air quality data uploaded by multiple air quality detection apparatuses. When receiving the air quality data, the server further receives base identifiers corresponding to the air quality data, so as to distinguish between and learn the air quality data uploaded by the air quality detection apparatuses.

Step 504: Parse the air quality data, to obtain air indicator data collected by one or more air quality sensors in a detachable sensor component that is connected to a base in the air quality detection apparatus.

In this embodiment, after obtaining the air quality data, the server parses the data, to obtain the air indicator data that is included in the data and that is collected by the one or more air quality sensors in the detachable sensor component connected to the base in the air quality detection apparatus. For example, the server obtains, by means of parsing, air temperature information collected by a detached temperature sensor in the air quality detection apparatus. The air temperature information reflects a detected temperature of air around the air quality detection apparatus.

Further, the server can further determine, according to a related air quality evaluation standard, an air quality status reflected by each piece of air indicator data. Specifically, multiple thresholds may be set for each air quality indicator. When corresponding air indicator data obtained by means of parsing falls within a range between two neighboring thresholds, correspondingly, specific air quality status information indicated by the corresponding air indicator data is determined. For example, when an AQI index obtained by means of parsing is 34, it indicates that air quality is excellent; when the AQI index obtained by means of parsing is 134, it indicates that the air quality is lightly polluted; and when it is obtained by parsing that a temperature is 32° C. and humidity is 80%, it indicates that the weather is wet and hot.

Step 506: Store the base identifier and the corresponding one or more pieces of air indicator data.

Specifically, the server stores the received base identifier and the corresponding one or more pieces of air indicator data obtained by means of parsing. Further, the server further stores a time point at which the base identifier and the corresponding one or more pieces of air indicator data are received. In addition, the stored time point, the base identifier, and the one or more pieces of air indicator data are associated, so that the server can distinguish, according to the association information, between the stored air indicator data that is detected by air quality detection apparatuses and time points at which the data is detected.

In this embodiment, the server receives, parses, and stores air quality data detected by the air quality detection apparatuses, thereby lowering a hardware requirement on an air quality detection apparatus, and reducing costs of the air quality detection apparatus. In addition, because the air quality data is stored in the server, it is convenient for a user to obtain, by using the server that is connected to a terminal through a network, real-time air quality data and history air quality data that are detected by an air quality detection apparatus bound to the server, thereby improving the use flexibility of the user.

In some embodiments, the air quality data includes protocol header data, a quantity of pieces of air indicator data, and at least one piece of air indicator data.

In this embodiment, the protocol header data is generally a piece of fixed data, so that when receiving the air quality data, the server can rapidly locate a communication protocol of the air quality data according to the protocol header data. The quantity of pieces of air indicator data is used for indicating a quantity of pieces of detected air indicator data that are included in the air quality data.

In some embodiments, in addition to the protocol header data, the quantity of pieces of air indicator data, and the at least one piece of air indicator data, the air quality data further includes parity data. Before the step of storing the base identifier and the corresponding one or more pieces of air indicator data, the air quality data processing method further includes: generating authentication data according to the quantity of pieces of air indicator data and the at least one piece of air indicator data; and comparing the authentication data with the parity data, and if the authentication data is consistent with the parity data, entering the step of storing the base identifier and the corresponding one or more pieces of air indicator data, or if the authentication data is not consistent with the parity data, performing no processing.

In this embodiment, after obtaining the air quality data including the parity data, the server generates, by using the totally same preset method as that used by the air quality detection apparatus, the authentication data corresponding to the parity data. That is, the server generates the authentication data according to the quantity of pieces of air indicator data and the at least one piece of air indicator data in the received air quality data. Preferably, a bit-by-bit XOR operation may be performed on the quantity of pieces of air indicator data and all the pieces of air indicator data in the received air quality data, to obtain the authentication data.

The generated authentication data is compared with the parity data in the received air quality data. If the authentication data is totally the same as the parity data, it indicates that the received air quality data is not damaged during transmission, and the base identifier and the corresponding one or more pieces of air indicator data are stored. If the authentication data is different from the parity data, it indicates that the received air quality data is different from the air quality data sent by the air quality detection apparatus. That is, packet loss of the air quality data may occur during transmission. Therefore, the received air quality data is discarded, and is not processed.

In this embodiment, the generated authentication data is compared with the parity data, and it can be learned, according to a comparison result, whether the received air quality data is complete, so as to ensure the accuracy of the air quality data.

In some embodiments, the air quality data processing method further includes: obtaining a stored user identifier corresponding to the base identifier; and sending the one or more pieces of air indicator data that correspond to the base identifier to a terminal corresponding to the user identifier.

In this embodiment, the server may further obtain the preset user identifier corresponding to the base identifier. The user identifier may be information of an account registered by a user. The user may register the account by using the terminal, and may set that the user identifier is in association with one or more base identifiers, so that the account is bound to a corresponding air quality detection apparatus. According to a correspondence between the user identifier and the base identifier, the user identifier may be in association with air quality data corresponding to the base identifier.

The server may send, in real time, the one or more pieces of air indicator data that correspond to the base identifier to the terminal corresponding to the user identifier. Further, air quality status information reflected by the air indicator data is further sent to the terminal corresponding to the user identifier.

Still further, if corresponding air quality status information that is reflected by the one or more pieces of air indicator data obtained by means of parsing reaches a hazardous level, the server may further send warning information to the terminal while sending the corresponding air quality status information reflected by the air indicator data to the terminal corresponding to the user identifier. For example, when detecting that a current temperature is 45° C., after determining that air quality status information is that the current temperature is extremely high, the server further sends warning information such as "The current temperature is extremely high, please take measures for heatstroke prevention" to the terminal. Specifically, the server may deliver the warning information to the terminal by sending an SMS message.

In this embodiment, the server can deliver, in real time, the air indicator data collected by the air quality detection apparatus to the terminal, so that a user can learn an air quality status in time. This is quite practical and convenient in use.

In some embodiments, the air quality data processing method further includes: receiving a query instruction sent by a terminal, the query instruction carrying a user identifier; querying a corresponding base identifier according to the user identifier; and returning, to the terminal, one or more pieces of air indicator data that correspond to the found base identifier.

In this embodiment, the terminal may send the query instruction to the server, to query related air quality information detected by one or more air quality detection apparatuses that are bound by a user. For example, current single temperature information, and information of formaldehyde content or information of PM 2.5 content in the air may be queried. Alternatively, one or more types of information such as temperature information and information of formaldehyde content or information of PM 2.5 content in the air in a time period may be queried.

The query instruction initiated by the terminal carries the user identifier. The server receives the query instruction, obtains the user identifier by means of parsing, and further finds, according to information of association between the user identifier and a base identifier of an air quality detection apparatus, the base identifier corresponding to the user identifier. The server returns, to the terminal, the one or more pieces of air indicator data that correspond to the found base identifier. Specifically, the server sends, according to a specific query command in the query instruction, information related to the query command in air quality data that is uploaded by a corresponding air quality detection apparatus and that is stored in the server, to the terminal. That is, the user may query, by using the terminal and according to a requirement, various types of air quality data that are in different time periods and that are detected by the air quality detection apparatus bound by the user.

Based on the above, in some embodiments, a method of processing air quality data, includes: at a processing unit of a first air quality monitoring station, wherein the processing unit has one or more processors and memory: receiving air indicator data collected by one or more air quality sensors, wherein the one or more air quality sensors are detachably coupled to a hardware base of the air quality monitoring station via one or more data communication interfaces, and the hardware base is communicably coupled to a remote server over a network; generating air quality data according to the air indicator data, wherein the air quality data is derived from air indicator data received from one or more air quality sensors over a distance traveled by the one or more air quality sensors; and sending the air quality data, via the hardware base, to the remote server.

In some embodiments, the method includes: generating a data collection schedule for each of the one or more air quality sensors based on the air indicator data collected by the one or more air quality sensors, wherein a frequency of data collection for a respective air quality sensor in the data collection schedule for the air quality sensor is based at least in part on a rate of change in air quality data received from the respective air quality sensor. For example, if the CO2 indicator does not vary quickly along the route when the vehicle is driving, the CO2 sensor can collect or send data at a lower frequency than another air quality indicator, such as PM2.5. In some embodiments, a low danger indicator (e.g., temperature, CO2 content, etc.) can have a lower collection frequency than a high danger indicator (e.g., Carbon Monoxide (CO) content, or other poisonous gas indicators).

In some embodiments, generating different data collection schedules for a respective air quality sensor of the one or more air quality sensors based at least in part on different routes taken by the respective air quality sensor, including a first data collection schedule with a first data collection frequency for a first route taken by the respective air quality sensor, and a second data collection schedule with a second data collection frequency for a second route, different from the first route, taken by the respective air quality sensor. In some embodiments, generating a data collection schedule for a respective air quality sensor of the one or more air quality sensors, wherein the data collection schedule specifies a first data collection frequency for a first portion of a route taken by the respective air quality sensor, and specifies a second data collection frequency that is different from the first data collection frequency for a second portion of the route that is different from the first portion of the route. For example, GPS information is associated with the air indicator data and the air quality data that is collected along a particular route as the vehicle carrying the air quality monitoring station is traveling along the route. If the vehicle travels along the route multiple times, the air quality data and air indicator data for each portion of the route are correlated to produce an overall air condition of the geographic region near that portion of the route, and air quality inside the vehicle on the corresponding portions of the route. The historic data can be used as the basis for determining the data collection frequencies for the different types of air indicators. In some embodiments, historic data collected by other air quality monitoring stations carried by other vehicles traveling on the same portions of the route are also taken into consideration when determining the data collection schedule of the different types of air quality sensors.

In some embodiments, generating the data collection schedule for the respective air quality sensor of the one or more air quality sensors include: selecting the first data collection frequency and the second data collection frequency based at least in part on historic air indicator data previously collected on the route (based on location, trend, data change range, etc.). In some embodiments, the historic air indicator data previously collected on the route include data collected by the respective air quality sensor and data collected by air quality sensors other than the respective air quality sensor.

In some embodiments, the method includes: receiving integrated air quality data from the remote server, wherein the integrated air quality data is derived from the air quality data submitted to the remote server by the first air quality monitoring station and one or more second air quality monitoring stations that are distinct from the first air quality monitoring stations, wherein the integrated air quality data combines the air quality data from the first air quality monitoring station and the one or more second air quality monitoring stations associated with the same geographic region.

In some embodiments, a first sensor of the one or more sensors collects data on a first set of air quality indicators, and a second sensor of the one or more sensors collects data on a second set of air quality indicators, the first set and the second set of air quality indicators includes at least one common indicator. For example, both sensors collect temperature information and PM2.5 information, in addition to other sensor specific indicators (e.g., the first sensor collects CO content, while the second sensor collects $SO_2$ content). In some embodiments, the processing unit integrates the indicator values for the same indicator from the different sensors (e.g., take an average, or discards outliers, discard low precision values when high precision values are available).

In some embodiments, when new sensor components are installed onto the base, the processing unit provides a data collection schedule to the new sensor based on the data collection schedule of other sensors, e.g., to balance processing load, data transmission bandwidth, and to maximum data correlation (e.g., based on location and time) between the data from different sensors.

In some embodiments, the processing unit generates alerts for adjusting air quality control based on the air quality data that is generated locally, and/or integrated air quality data that is downloaded from the server. In some embodiments, the processing unit receives a prediction of air quality for an upcoming portion of the route that the air quality monitoring station is traveling on (e.g., based on historic data collected on this portion of the route by the air quality monitoring station and by optionally, by other air quality monitoring stations also traveling or traveled on this portion of the route), and generates an alert for the user if the air quality is below a predefined standard. In some embodiments, the processing unit issues an instruction to the vehicle control to adjust the air quality controls available on the vehicle, such as opening/closing a window, activate a particular air filter, turning on the air conditioner, switching between gas engine and electric engine of the vehicle, etc.

In some embodiments, the processing unit makes the prediction of air quality for both in-vehicle condition, and out-of-vehicle conditions, and suggests routes based on both distance, traffic, as well as air quality along the different possible routes. In some embodiments, the processing unit makes predictions of air quality based on traffic conditions and time for each route when suggesting directions to the user for a particular destination, in addition to the air quality data collected from the sensors.

Other details of the method, apparatus, and systems are disclosed in other parts of the present disclosure, and may be combined with the features disclosed herein without specific limitation, and thus are not repeated herein.

An embodiment of the present technology further provides a server. An internal structure of the server may correspond to the structure shown in FIG. 3A or FIG. 3B. Each of the following modules may be wholly or partially implemented by using software, hardware, or a combination of the software and the hardware.

Figure 6:
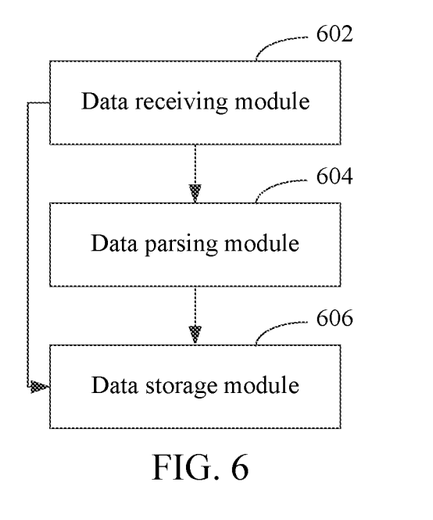
FIG. 6 is a structural block diagram of a server according to some embodiments.

In some embodiments, as shown in FIG. 6, the server in this embodiment includes a data receiving module 602, a data parsing module 604, and a data storage module 606.

The data receiving module 602 is configured to receive air quality data and a corresponding base identifier that are uploaded by an air quality detection apparatus.

The data parsing module 604 is configured to: parse the air quality data, to obtain air indicator data collected by one or more air quality sensors in a detachable sensor component that is connected to a base in the air quality detection apparatus. The data storage module 606 is configured to store the base identifier and the corresponding one or more pieces of air indicator data.

In some embodiments, the air quality data includes: protocol header data, a quantity of pieces of air indicator data, and at least one piece of air indicator data.

In some embodiments, the air quality data further includes parity data. The data parsing module 604 is further configured to: generate authentication data according to the quantity of pieces of air indicator data and the at least one piece of air indicator data; and compare the authentication data with the parity data, and if the authentication data is consistent with the parity data, call the data storage module 606 to store the base identifier and the corresponding one or more pieces of air indicator data, or if the authentication data is not consistent with the parity data, perform no processing.

Figure 7:
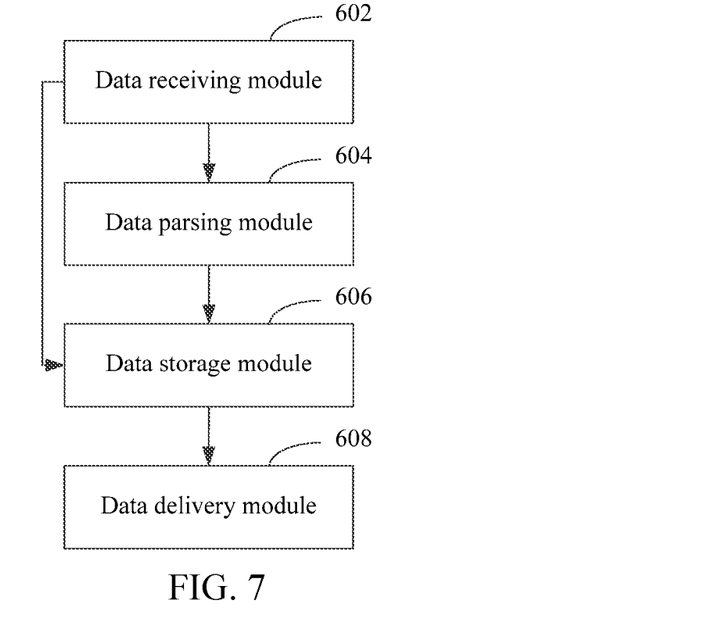
FIG. 7 is a structural block diagram of a server according to some embodiments.

In some embodiments, as shown in FIG. 7, the server in this embodiment further includes a data delivery module 608.

The data delivery module 608 is configured to: obtain a stored user identifier corresponding to the base identifier; and send the one or more pieces of air indicator data that correspond to the base identifier to a terminal corresponding to the user identifier.

Figure 8:
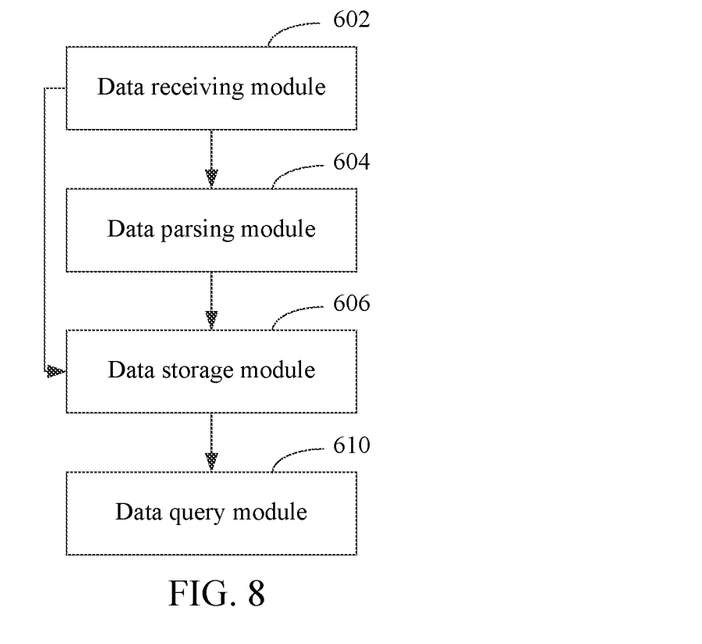
FIG. 8 is a structural block diagram of a server according to some embodiments.

In some embodiments, as shown in FIG. 8, another air quality data processing apparatus is provided. In this embodiment, the server further includes a data query module 610.

The data query module 610 is configured to: receive a query instruction sent by a terminal, the query instruction carrying a user identifier; query a corresponding base identifier according to the user identifier; and return, to the terminal, one or more pieces of air indicator data that correspond to the found base identifier.

A person of ordinary skill in the art may understand that all or some of the processes of the methods in the embodiments may be implemented by a computer program instructing relevant hardware. The program may be stored in a computer readable storage medium. When the program runs, the processes of the methods in the embodiments are performed. The foregoing storage medium may include: a magnetic disk, an optical disc, a read-only memory (ROM), or a random access memory (RAM).

The foregoing embodiments merely describe a few implementations of the present disclosure, and the description is relatively specific and detailed, but shall not be construed as a limit to the patent scope of the present disclosure. It should be noted that, a person of ordinary skill in the art may make, without departing from the concept of the present disclosure, several deformations and improvements that belong to the protection scope of the present disclosure. Therefore, the protection scope of the patent of the present disclosure shall be subject to the appended claims.

What is claimed is:
1. A method of processing air quality data, comprising:
at a processing unit of a first air quality monitoring station, wherein the processing unit has one or more processors and memory and the first air quality monitoring station is located inside a vehicle:
receiving air indicator data collected by a plurality of air quality sensors, each monitoring a distinct parameter, wherein the air indicator data reflects air quality in the vehicle and the plurality of air quality sensors are selected according to a user's requirement and are detachably coupled to a hardware base of the first air quality monitoring station via one or more data communication interfaces, and the hardware base is communicably coupled to a remote server over a network;

based on the air indicator data:
  generating air quality data according to the air indicator data, wherein the air quality data is derived from the air indicator data collected by the plurality of air quality sensors over a distance traveled by the air quality sensors;
  for each of the plurality of air quality sensors, generating a respective data collection schedule for a respective air quality sensor based on the air indicator data collected by the respective air quality sensor, wherein the respective data collection schedule includes a data collection frequency for the respective air quality sensor that is based at least in part on: (i) a travel route of the respective air quality sensor and (ii) historic air quality data corresponding to the parameter monitored by the respective air quality sensor that is collected along the travel route and stored on the remote server;
  sending the air quality data, via the hardware base, to the remote server, wherein the server is configured to transmit the air quality data to a user terminal and cause display of the air quality data on the user terminal; and
  recommending an upcoming travel route for the vehicle according to a prediction of the air quality data along the upcoming travel route based on the historic air quality data collected along the travel route by the remote server and GPS information that is associated with the air indicator data.

2. The method of claim 1, wherein the air quality sensors include a first air quality sensor, the method further comprising:
  generating, for the first air quality sensor, (i) a first data collection schedule with a first data collection frequency for a first route taken by the first air quality sensor and (ii) a second data collection schedule with a second data collection frequency for a second route, different from the first route, taken by the first air quality sensor.

3. The method of claim 1, wherein the air quality sensors include a first air quality sensor, the method further comprising:
  generating, for the first air quality sensor, a data collection schedule that specifies a first data collection frequency for a first portion of a route taken by the first air quality sensor and specifies a second data collection frequency for a second portion of the route taken by the first air quality sensor, wherein the first data collection frequency is distinct from the second data collection frequency and the first portion of the route is distinct from the second portion of the route.

4. The method of claim 3, wherein the first data collection frequency and the second data collection frequency are selected based at least in part on the historic air indicator data previously collected on the route.

5. The method of claim 4, wherein the historic air indicator data previously collected on the route include data collected by the respective air quality sensor and data collected by air quality sensors other than the respective air quality sensor.

6. The method of claim 1, further comprising:
  receiving integrated air quality data from the remote server, wherein the integrated air quality data is derived from the air quality data submitted to the remote server by the first air quality monitoring station and one or more second air quality monitoring stations that are distinct from the first air quality monitoring stations, wherein the integrated air quality data combines the air quality data from the first air quality monitoring station and the one or more second air quality monitoring stations associated with the same geographic region.

7. A system of processing air quality data, comprising:
a processing unit of a first air quality monitoring station that is located inside a vehicle, wherein the processing unit has one or more processors and memory, the memory storing instructions, which when executed by the one or more processors, cause the processors to perform operations comprising:
  receiving air indicator data collected by a plurality of air quality sensors, each monitoring a distinct parameter, wherein the air indicator data reflects air quality in the vehicle and the plurality of air quality sensors are selected according to a user's requirement and are detachably coupled to a hardware base of the first air quality monitoring station via one or more data communication interfaces, and the hardware base is communicably coupled to a remote server over a network;
  based on the air indicator data:
    generating air quality data according to the air indicator data, wherein the air quality data is derived from the air indicator data collected by the plurality of air quality sensors over a distance traveled by the air quality sensors;
    for each of the plurality of air quality sensors, generating a respective data collection schedule for a respective air quality sensor based on the air indicator data collected by the respective air quality sensor, wherein the respective data collection schedule includes a data collection frequency for the respective air quality sensor that is based at least in part on: (i) a travel route of the respective air quality sensor and (ii) historic air quality data corresponding to the parameter monitored by the respective air quality sensor that is collected along the travel route and stored on the remote server;
    sending the air quality data, via the hardware base, to the remote server, wherein the server is configured to transmit the air quality data to a user terminal and cause display of the air quality data on the user terminal; and recommending an upcoming travel route for the vehicle according to a prediction of the air quality data along the upcoming travel route based on historic air quality data collected along the travel route by the remote server and GPS information that is associated with the air indicator data.

8. The system of claim 7, wherein the air quality sensors include a first air quality sensor, the operations further comprising:
  generating, for the first air quality sensor, (i) a first data collection schedule with a first data collection frequency for a first route taken by the first air quality sensor and (ii) a second data collection schedule with a second data collection frequency for a second route, different from the first route, taken by the first air quality sensor.

9. The system of claim 7, wherein the air quality sensors include a first air quality sensor, the operations further comprising:
  generating, for the first air quality sensor, a data collection schedule that specifies a first data collection frequency for a first portion of a route taken by the first air quality sensor and specifies a second data collection frequency for a second portion of the route taken by the first air quality sensor, wherein the first data collection frequency is distinct from the second data collection frequency and the first portion of the route is distinct from the second portion of the route.

10. The system of claim 9, wherein the first data collection frequency and the second data collection frequency are selected based at least in part on the historic air indicator data previously collected on the route.

11. The system of claim 10, wherein the historic air indicator data previously collected on the route include data collected by the respective air quality sensor and data collected by air quality sensors other than the respective air quality sensor.

12. The system of claim 7, wherein the operations further comprise:
receiving integrated air quality data from the remote server, wherein the integrated air quality data is derived from the air quality data submitted to the remote server by the first air quality monitoring station and one or more second air quality monitoring stations that are distinct from the first air quality monitoring stations, wherein the integrated air quality data combines the air quality data from the first air quality monitoring station and the one or more second air quality monitoring stations associated with the same geographic region.

13. A non-transitory computer-readable storage medium storing instructions, the instructions, when executed by one or more processors of a processing unit of a first air quality monitoring station that is located inside a vehicle, cause the processing unit to perform operations comprising:
receiving air indicator data collected by a plurality of air quality sensors, each monitoring a distinct parameter, wherein the air indicator data reflects air quality in the vehicle and the plurality of air quality sensors are selected according to a user's requirement and are detachably coupled to a hardware base of the first air quality monitoring station via one or more data communication interfaces, and the hardware base is communicably coupled to a remote server over a network;
based on the air indicator data:
generating air quality data according to the air indicator data, wherein the air quality data is derived from the air indicator data collected by the plurality of air quality sensors over a distance traveled by the air quality sensors;
for each of the plurality of air quality sensors, generating a respective data collection schedule for a respective air quality sensor based on the air indicator data collected by the respective air quality sensor, wherein the respective data collection schedule includes a data collection frequency for the respective air quality sensor that is based at least in part on: (i) a travel route of the respective air quality sensor and (ii) historic air quality data corresponding to the parameter monitored by the respective air quality sensor that is collected along the travel route and stored on the remote server;
sending the air quality data, via the hardware base, to the remote server, wherein the server is configured to transmit the air quality data to a user terminal and cause display of the air quality data on the user terminal; and
recommending an upcoming travel route for the vehicle according to a prediction of the air quality data along the upcoming travel route based on historic air quality data collected along the travel route by the remote server and GPS information that is associated with the air indicator data.

14. The non-transitory computer-readable storage medium of claim 13, wherein the air quality sensors include a first air quality sensor, the operations further comprising:
generating, for the first air quality sensor, (i) a first data collection schedule with a first data collection frequency for a first route taken by the first air quality sensor and (ii) a second data collection schedule with a second data collection frequency for a second route, different from the first route, taken by the first air quality sensor.

15. The non-transitory computer-readable storage medium of claim 13, wherein the air quality sensors include a first air quality sensor, the operations further comprising:
generating, for the first air quality sensor, a data collection schedule that specifies a first data collection frequency for a first portion of a route taken by the first air quality sensor and specifies a second data collection frequency for a second portion of the route taken by the first air quality sensor, wherein the first data collection frequency is distinct from the second data collection frequency and the first portion of the route is distinct from the second portion of the route.

16. The non-transitory computer-readable storage medium of claim 15, wherein the first data collection frequency and the second data collection frequency are selected based at least in part on the historic air indicator data previously collected on the route.

17. The non-transitory computer-readable storage medium of claim 16, wherein the historic air indicator data previously collected on the route include data collected by the respective air quality sensor and data collected by air quality sensors other than the respective air quality sensor.

* * * * *